US007422893B2

(12) United States Patent
Diresta et al.

(10) Patent No.: US 7,422,893 B2
(45) Date of Patent: Sep. 9, 2008

(54) APPARATUS FOR GROWING CELLS UNDER VARIABLE HYDROSTATIC PRESSURES

(75) Inventors: Gene R. Diresta, Pleasantville, NY (US); John H. Healey, New York, NY (US); Robert Schwar, Forestburgh, NY (US)

(73) Assignee: Memorial Sloan-Kettering Cancer Center, New York, NY (US)

( * ) Notice: Subject to any disclaimer, the term of this patent is extended or adjusted under 35 U.S.C. 154(b) by 801 days.

(21) Appl. No.: 10/378,585

(22) Filed: Mar. 3, 2003

(65) Prior Publication Data

US 2003/0211600 A1 Nov. 13, 2003

Related U.S. Application Data

(60) Provisional application No. 60/360,976, filed on Mar. 1, 2002.

(51) Int. Cl.
*C12M 1/00* (2006.01)
*C12M 3/00* (2006.01)

(52) U.S. Cl. ............. 435/289.1; 435/325; 435/283.1; 435/304.1; 435/305.1

(58) Field of Classification Search ............. 435/325, 435/283.1, 289.1, 304.1, 305.1
See application file for complete search history.

(56) References Cited

U.S. PATENT DOCUMENTS 4,833,089 A * 5/1989 Kojima et al. ............ 435/286.6
4,851,354 A * 7/1989 Winston et al. ............. 435/402

OTHER PUBLICATIONS

Ute Hansen, Michael Schumke, Christian Domm, Niki Ioannidis, Joachim Hassenpflug, Thorsten Gehrke, Bodo Kurz. "Combination of reduced oxygen tension and intermittent hydrostatic pressure: a useful tool in articular cartilage tissue engineering," Journal of Biomechanics 34, 941-949 (2001). [Exhibit 1].
Cornelia Hasel, Susanne Durr, Silke Bruderlein, Ingo Melzner, Peter Moller. "A cell-culture system for long-term maintenance of elevated hydrostatic pressure with the option of additional tension," Journal of Biomechanics 35, 579-584 (2002). [Exhibit 2].
Jenneke Klein-Nulend, Jan Roelofsen, Cornelis M. Semeins, Antonius L.J.J. Bronkers, and Elisabeth H. Burger. "Mechanical Stimulation of Osteopontin mRNA Expression and Synthesis in Bone Cell Cultures," Journal of Cellular Physiology 170, 174-181 (1997). [Exhibit 3].
Thomas D. Brown. "Techniques for mechanical stimulation of cells in vitro: a review," Journal of Biomechanics 33, 3-14 (2000). [Exhibit 4].
Salwen SA, Szarowski DH, Turner JN, Bizios R. "Three-dimensional changes of the cytoskeleton of vascular endothelial cells exposed to sustained hydrostatic pressure," Medical and Biological Engineering and Computing, 36(4), 520-527 (1998). [Exhibit 5].

Nagatomi J, Arulanandam BP, Metzger DW, Meuniera, Bizios R. "Frequency- and duration-dependent effects of cyclic pressure on select bone cell functions," Tissue Engineering, 7(6), 717-728 (2001). [Exhibit 6].
Mitchell SB, Sanders JE, Garbini JL, Schuessler PK. "A device to apply user-specified strains to biomaterials in culture," IEEE Trans Biomed Eng 48 (2), 268-273, (2001). [Exhibit 7].
Ozawa H, Imamura K, Abe E, Takahashi N, Hiraide T, Shibasaki Y, Fukuhara T, Suda T. "Effect of a continuously applied compressive pressure on mouse osteoblast-like cells (MC3T3-E1) in vitro," Journal of Cellular Physiology, 142(1), 177-185 (1990). [Exhibit 8].
Saito S, Ngan P, Rosol T, Saito M, Shimizu H, Shinjo N, Shanfeld J, Davidovitch Z. "Involvement of PGE synthesis in the effect of intermittent pressure and Interleukin-1 β on bone resorption," J Dent Res Jan, 70(1), 27-33 (1990). [Exhibit 9].
Takano-Yamamoto T, Soma S, Nakagawa K, Kobayashi Y, Kawakami M, Sukuda M. "Comparison of the effects of hydrostatic compressive force on glycosaminoglycan synthesis and proliferation in rabbit chondrocytes from mandiblar condylar cartilage, nasal septum, and spheno-occipital synchondrosis in vitro," Am J Orthod Dentofacial Orthop, 99(5), 448-55 (1991). [Exhibit 10].
Koyama S, Miwa T, Sato T, Aizawa M. "Optical chamber system designed for microscopic observation of living cells under extremely high hydrostatic pressure," Extremophiles Dec, 5(6), 409-15, (2001), [Exhibit 11].
Kaarniranta K, Elo MA, Sironen RK, Karjalainen HM, Helminen HJ, Lammi MJ. "Stress responses of mammalian cells to high hydrostatic pressure," Biorheology 40, 87-92 (2003). [Exhibit 12].
Tezel J G, Wax MB. "Increased production of tumor necrosis factor-alpha by glial cells exposed to simulated ischemia or elevated hydrostatic pressure induces apoptosis in cocultured retinal ganglion cells," The Journal of Neuroscience. 20(23), 8693-700, Dec. 1, 2000. [Exhibit 13].
Nerucci F, Fioravanti A, Cicero MR, Marcolongo K, SpiHaset C, Durr S, Bruderlein S, Melzner I, Moller P. "Preparation of a pressurization system to study the effect off a hydrostatic pressure on chondrocyte cultures," In Vitro Cellular & Developmental Biology. Animal 34: Jan. 9-10, 1998. [Exhibit 14].
Wax Mb, Tezet G, Kobayashi S, Hernandez MR. "Responses of different cell lines from ocular tissues to elevated hydrostatic pressure," Br J Ophthalmol 84, 423-428 (2000). [Exhibit 15].
Saris DB, Sanyal A, An KN, Fitzsimmons JS, O'Driscoll SW. "Periosteum responds to dynamic fluid pressure by proliferating in vitro," Journal of Orthopaedic Research 17(5), 668-677 (1999). [Exhibit 16].

(Continued)

*Primary Examiner*—Leon B. Lankford, Jr.
*Assistant Examiner*—Susan E. Fernandez
(74) *Attorney, Agent, or Firm*—Law Offices of Albert Wai-Kit Chan, PLLC (57) ABSTRACT

An apparatus for growing cells in a 2-D cell cassette having a matrix for cell growth under pressure comprising two side assemblies which include a frame with a rigid support that fits over the 2-D cell cassette, with said assemblies positioned on either side of the cassette over the solid support sides, and a means to secure the sides of the cassette. The invention also provides different uses of this apparatus.

16 Claims, 10 Drawing Sheets

OTHER PUBLICATIONS

Suh JK, Baek GH, Aroen A, Malin CM, Niyibizi C, Evans CH, Westerhausen-Larson A. "Intermittent sub-ambient interstitial hydrostatic pressure as a potential mechanical stimulator for chondrocyte metabolism," Osteoarthritis Cartilag, 7(1) :71-80 (1999). [Exhibit 17].

Carver SE, Heath CA. "Semi-continuous perfusion system for delivering intermittent physiological pressure to regenerating cartilage," Tissue Engineering 5(1), 1-11 (1999). [Exhibit 18].

Hartig M, Ulrich J, Haas-Peter Wiesmann. "Capacitively coupled electric fields accelerate proliferation of osteoblast-like primary cells and increase bone extracellular matrix formation in vitro," Eur. Biophys J 29, 499-506 (2000). [Exhibit 19].

Brighton CT, Wang W, Seldes R, Zhang G. and Pollack S. "Signal Transduction in Electrically Stimulated Bone Cells," JBJS 83 A (10): 1514-23, (2001). [Exhibit 20].

Hiroyuki Ozawa, Etsuko Abe, Yoshinobu Shibasaki, Tatsuo Fukuhara, and Tatsuo Suda. "Electric Fields Stimulate DNA Synthesis of Mouse Osteoblast-Like Cells (MC3T3-E1) by a Mechanism Involving Calcium Ions," Journal of Cellular Physiology 138:477-483 (1989). [Exhibit 21].

Peter F. Armstrong, Carl T. Brighton, and Andrew M. Star. "Capacitively Coupled Electrical Stimulation of Bovine Growth Plate Chondrocytes Grown in Pellet Form," Journal Orthopaedic Research 6:265-271, (1988). [Exhibit 22].

Gunter Fuhr, Henning Glasser, Torsten Muller, Thomas Schnelle. "Cell manipulation and cultivation under a.c. electric field influence in highly conductive culture media," Biochimica et Biophysica Acta 1201, 353-360 (1994) [Exhibit 23].

Carl T. Brighton, M.D., PH.D., Enyi Okereke, M.D., Solomon R. Pollack, PH.D., Charles C. Clark, PH.D. "In Vitro Bone-Cell Response to a Capacitively Coupled Electrical Field," Clinical Orthopaedics and Related Research. No. 285, 255-62 (1992). [Exhibit 24].

Korenstein R. Somjen D. Fischler H. Binderman I. "Capacitative pulsed electric stimulation of bone cells induction of cyclic amp changes and DNA synthesis," Biochimica et Biophysica Acta. 803(4):302-7 (1984). [Exhibit 25].

Karen M. Haberstroh, Martin Kaefer, Natacha DePaola, Sarah A. Frommer, Rena Bizios. A Novel In-Vitro System for the Simultaneous Exposure of Bladder Smooth Muscle Cells to Mechanical Strain and Sustained Hydrostatic Pressure, Journal of Biomechanical Engineering 124, 208-213 (2002). [Exhibit 1].

U.S. Appl. No. 11/018,094, field Dec. 20, 2004, DiResta et al.

Office Action for Diresta et al., "Apparatus for growing cells under variable hydrostatic pressures", U.S. Appl. No. 11/018,094, filed Dec. 20, 2004, dated Oct. 10, 2007.

* cited by examiner

APPARATUS FOR GROWING CELLS UNDER VARIABLE HYDROSTATIC PRESSURES

This application claims priority of U.S. Ser. No. 60/360, 976, filed Mar. 1, 2002, the content of which is incorporated by reference hereinto this application.

Various references are referred to throughout this application. Disclosures of these publications in their entireties are hereby incorporated by reference into this application to more fully describe the state of the art to which this invention pertains.

This application was supported in part by a National Cancer Institute Core Grant No. 08748. Accordingly, The United States Government may have certain rights in this invention.

BACKGROUND OF THE INVENTION

Laboratory cell culture is a biological technique used to grow cells, bacteria, etc. under sterile conditions. It is typically performed using a petri dish or culture bottle filled with a small volume of nutrient media and placed within a temperature controlled, humidified incubator. The cells within the dish or bottle exchange gases with the ambient gas atmosphere within the incubator. It is a two dimensional (2-D) technology because cells typically grow on the bottom of the container or on the surface of the media.

2-D cell culture is a suitable approach for most cells and bacteria, and is used for growing solid tumor cells. The approach, however, does not simulate the in vivo conditions experienced by growing solid tumor cells because these cells grow under conditions of elevated interstitial fluid pressures. These pressures are typically equivalent to the pressures within the arterioles that are feeding the tumor's capillary network. In bone tumors, pressures exceeding 50 mmHg (gauge) have been observed. Further, the elevated pressures alter the genetic expressions of tumor cells. Thus when studying the behavior of solid tumor cells, i.e. their response to chemotherapeutic agents, cells grown using the traditional 2-D approach may not reflect the behavior of their in vivo counterparts because of the major differences between the growth conditions.

Attempts to culture cells under elevated pressure environments have utilized elevated gas pressure within the petri dish or culture bottle incubator to achieve the desired pressure. However, the problem with this approach is the growth media's gas content is equilibrated to that of the imposed incubator gas pressure. The dissolved gas content is thus higher than physiologic levels. While tumor interstitial fluid pressures are elevated, the gas content of the fluid is only equilibrated to one atmosphere because that is the pressure within the lung, the organ responsible for gas equilibration.

The cassette is a new approach to 2-D cell culture introduced by BioCrystal, Ltd. It consists of a thin plastic case with two gas permeable membranes and two rubber infusion ports. The cassette permits cell culture under conventional growth conditions in a fully enclosed chamber with rapid gas exchange and cell harvest. Its design, however, is not capable of tolerating the elevated pressures needed to culture tumor cells. Pressurization of the cassette media results in bulging of the membrane sides. The effects of bulging include changing the media volume and membrane thickness as a function of pressure, increasing the membranes' susceptibility to rupture, and increasing the diffusion path for gas exchange within the media.

SUMMARY OF INVENTION

This invention provides an apparatus for growing cells in a 2-D cell cassette having a matrix for cell growth under pressure comprising two side assemblies which include a frame with a rigid support that fits over the 2-D cell culture cassette, with said assemblies positioned on either side of the cassette over the solid support sides, and a means to secure the sides of the cassette.

This invention also provides a method of growing cells under static or variable pressure comprising steps of: (a) seeding said cells in the fluid growth media within cassette; (b) placing the cassette of step (a) into the above-described apparatus; and (c) applying static or dynamic hydrodynamic pressure via the side port on the cassette.

Finally, this invention provides a composition comprising cells grown by the above method. This invention also provides a composition comprising the extract of cells grown by the above method.

DETAILED DESCRIPTION OF THE FIGURES

FIG. 1. 2-D Cell Culture Cassette. This figure shows the high pressure adapter (HPA) 1. The HPA is composed of two side assemblies 2 which are mirror images of one another and join in a hinge 3, each assembly comprising a frame 4 around a rigid support 5. The sections are made from a machinable, heat-and moisture-resistant plastic. This plastic is also autoclavable. The hinge enables the HPA to fold over a 2-D cell culture cassette over the side that contains the two rubber access ports 6. These access ports can be further provided with luer valves or three-way valves. The HPA closure ends with contact to the cassette's membrane frame. The rigid support can be a stainless steel mesh that covers the exposed membrane window without making contact with the membrane until the cassette is pressurized. Pressurization is accomplished using media injected into the cassette via a needle into one of the rubber ports or via the pressure port of the modified 2-D cell culture cassette. The pressure is observed using a gauge on the other port or via a three-way valve. The HPA is held in place by inserting the cassette with the HPA into the HPA multi-cassette holder. For controlling pressurization, the side port is 20 the method of pressurization.

(FIG. 2A —top view; FIG. 2B —front view; FIG. 2C —side view; FIG. 2D —top perspective view).

FIG. 8. Effect of Mesh on SaOS Growth Rate.

FIG. 8C. Trial #1 shows cells per $cm^2$. This shows that the mesh covering Opticell does not compromise cell growth in the exposed area. This is the same data as in 8A expressed in unites of cells/$cm^2$ in the Opticell and Opticell with and without the High-Pressure Apparatus.

FIG. 9A. Study #1 shows total cell count. This baseline study compares cell growth using a standard T75 flask and cell growth using Opticell with and without the high-pressure apparatus (HPA).

FIG. 9B. Study #2 repeats Study #1.

FIG. 9C. Trial #1 shows cells per $cm^2$. This shows that the mesh covering Opticell does not compromise cell growth in the exposed area. This is the same data as in 9A expressed in unites of cells/$cm^2$ in the Opticell and Opticell with and without the high-pressure apparatus (HPA).

FIG. 9D. Trial #2 is a repeat of Trial #1. Same data as in 9B. No difference in cell count per $cm^2$ is observed in 9C and 9D.

FIG. 10. Oxygen Uptake Studies. This figure compares the mean oxygenation rate of the culture media within the 2-D cell culture cassette without high-pressure apparatus (HPA) (FIG. 10A) and with HPA (FIG. 10B). The rate of oxygenation is faster with an uncovered cassette.

DETAILED DESCRIPTION OF THE INVENTION

This invention provides an apparatus for growing cells under pressure comprising a 2-D cell cassette having a matrix for cell growth, two side assemblies which include a frame with a rigid support that fits over the 2-D cell culture cassette solid, with said assemblies positioned on either side of the cassette over the solid support sides, and a means to secure the sides of the cassette.

In an embodiment, the matrix for cell growth is a membrane. In a further embodiment, the membrane is a fiber-reinforced membrane. In a still further embodiment, the fiber is metal or organic based. The metals can be stainless steel, platinum, gold, titanium or other biocompatible metal.

In a separate embodiment, the matrix is composed of beads. In another embodiment, the matrix is nylon-based. As known in the art, a variety of matrices can be used in this invention.

In an embodiment of the above apparatus, the cassette contains a means to facilitate imposition of fluid pressure. In a further embodiment, the means is a valve side port.

In a separate embodiment, the rigid support of the apparatus contains mesh or external, raised lattice. The mesh or lattice may be made of plastic or stainless steel, platinum, gold, titanium or other biocompatible metal.

It is not necessary that the rigid support contain mesh but more importantly it is the coverage of the matrix on which the cells are growing. In an embodiment, the percentage of coverage of the matrix may be up to 20%. In another embodiment, the coverage is up to 50%. In a separate embodiment, the coverage is up to 70%.

In an embodiment connecting to each side frame is a valve support which mates with an infusion part.

The above described apparatus may be made of plastic or stainless steel or other materials which can withstand high or negative pressure, and the heats of sterilization or resist the oxidation of sterilizing gases.

Figure 1:
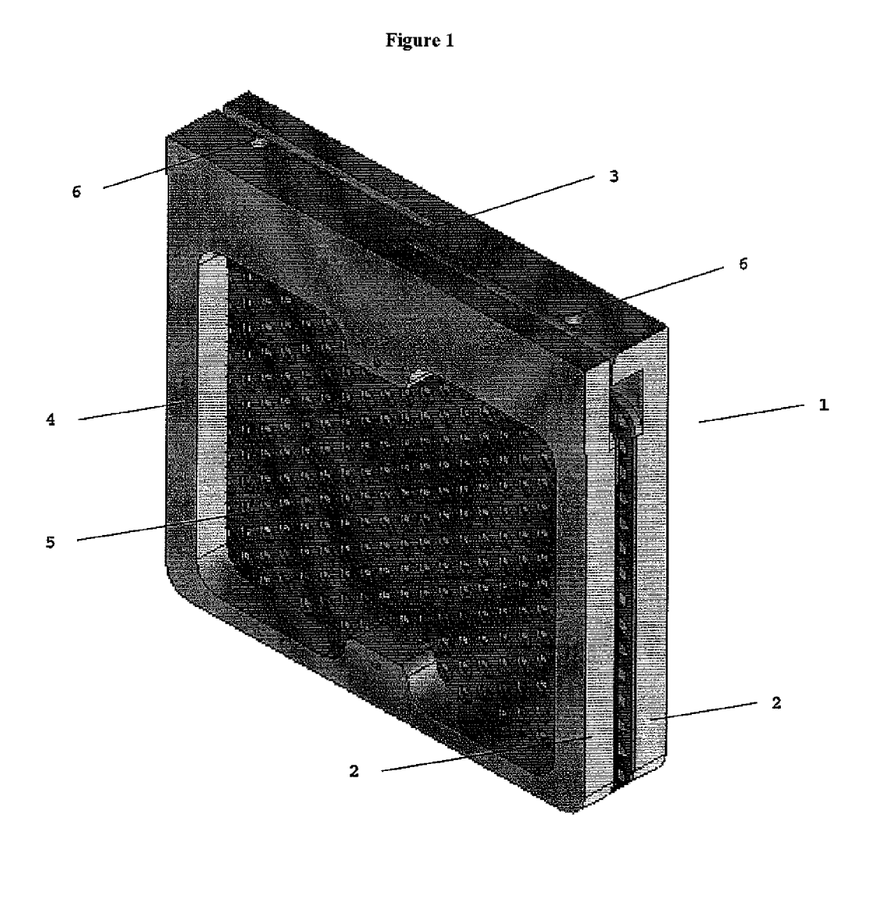

In an embodiment, the apparatus is depicted in FIG. 1.

This invention also provides a method of growing cells under static or variable pressure comprising steps of:
(a) seeding said cells in the fluid growth media within cassette;
(b) placing the cassette of step (a) into the above-described apparatus; and
(c) applying static or dynamic hydrodynamic pressure via the side port on the cassette.

The cells to be used in this invention include but are not limited to normal cells such as cartilage or muscle cells, bacteria, yeast, or various tumor cells. In an embodiment of the solid tumor cells, the tumor is an osteogenic sarcoma.

The static pressure ranges from negative to 100 mmHg and could be higher with appropriate rigid material. Appropriate pressures may be selected based on the physiologic cardiovascular pressure changes in arteries or veins.

This invention provides a composition comprising cells grown by the above method. This invention also provides a composition comprising the extract of cells grown by the above method.

When desirable, i.e. culture of electrically sensitive cells, an electric field can be applied across the membranes via the metal screen that supplies structural support for elevated pressure. The electrical potential is applied via electrical connection attached to the screen. Field strength depends upon cell type.

The invention will be better understood by reference to the Experimental Details which follow, but those skilled in the art will readily appreciate that the specific experiments detailed are only illustrative, and are not meant to limit the invention as described herein, which is defined by the claims which follow thereafter.

The invention disclosed herein refers to an adapter that is positioned over any 2-D cell cassette with gas permeable membrane sides to facilitate cell culture at elevated media pressures. The adapter comprises three components and is shown in FIG. 1. The components include two side assemblies that are positioned on either side of the cassette over the membrane sides. The side components include a frame with a rigid stainless steel mesh that fits above the 2-D cell culture cassette membrane and a valve support on the top of each side frame that mates with the infusion port. The mesh can be selected from a variety of openings. The adapter allows for movement of gas to the membrane and the application of pressure to the internal media without bulging the membrane ensuring a constant media volume. Further, the valve supports permit the secure location of two 3-way valves for communication with the media and application of pressure. The adapter can be made from rigid plastic, i.e. delrin, or metal, i.e. stainless steel.

Also disclosed herein is a new cassette design that includes a screen support over two membrane side windows to buttress the membrane for high pressure application. The screen can be made from the same material as the cassette frame or with stainless steel. The cassette design will also include two fluid entry port valves to facilitate flow through capability at elevated pressures without leakage. The intent is to duplicate the functionality of the adapter described above for low pressure 2-D cell culture with a new cassette expressly designed for 2-D high pressure cell culture. This high-pressure cassette integrates the essential features of the low pressure cassette adapter used to enable a low pressure cassette to function under high pressure conditions.

Figure 2:
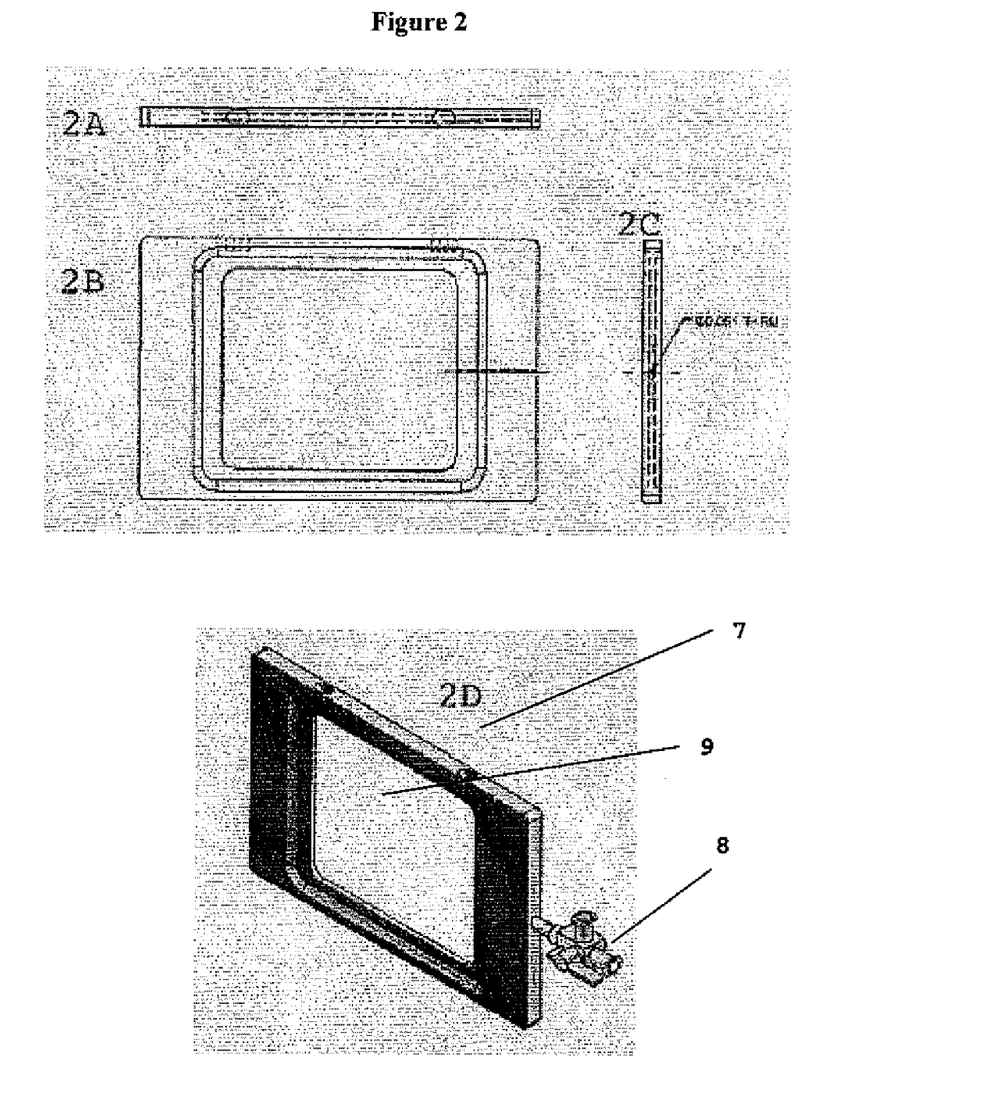
FIG. 2. 2-D Cell Culture Cassette Showing Pressurization Port. This figure is the modified 2-D cell culture cassette 7 showing side port with a three-way valve 8 machined along either of the short sides of cassette to facilitate pressurization of the cassette. The valve is normally closed unless pressurization is performed. It is intended for continuous pressurization. The cassette is a chamber with two gas-permeable membrane growth surfaces 9.
Figure 3:
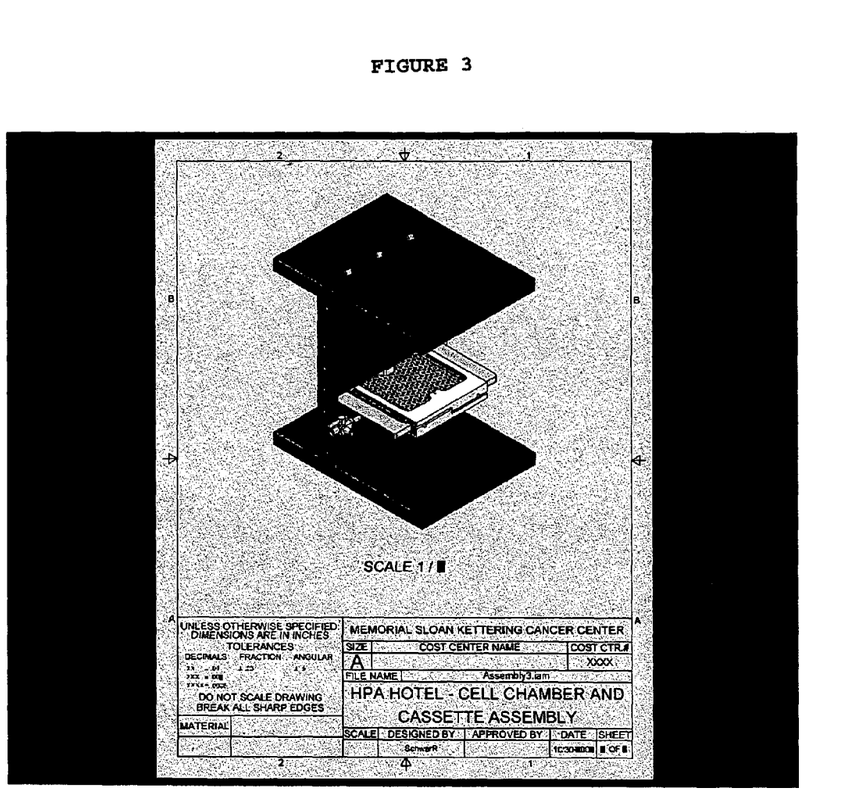
FIG. 3. Detail of the HPA multi-cassette holder. The holder in this figure is a plastic container dimensioned to hold up to six cassettes with HPAs in place. The cassette-HPA units are inserted into spaced groves at the base of the multi-cassette holder. The size of the multi-cassette holder can be fabricated to hold any number of assemblies. This figure shows the HPA correctly positioned over a modified 2D cell culture cassette within the holder.
Figure 4:
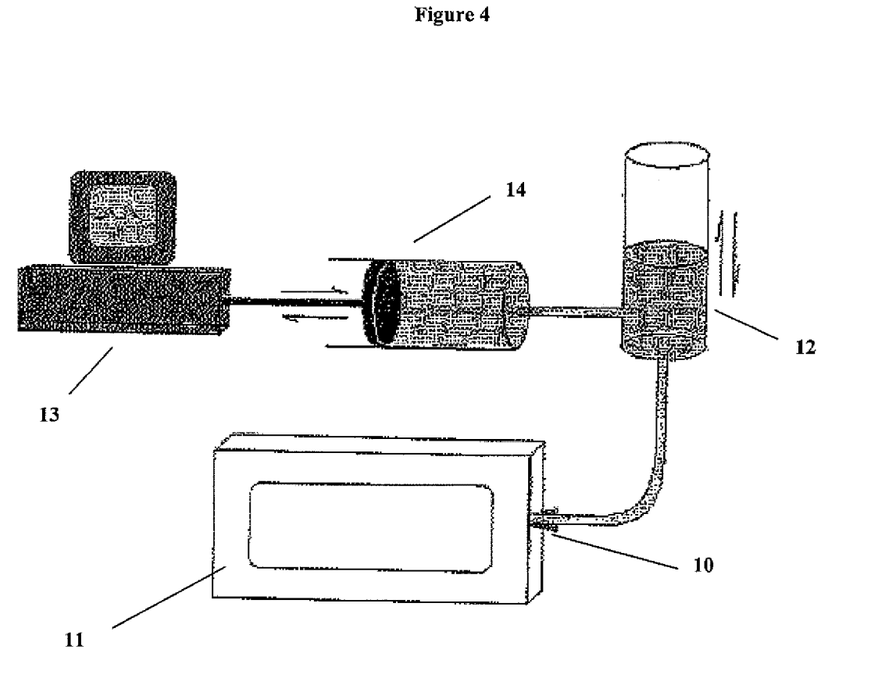
FIG. 4. Method for generating variable hydrostatic pressure within the cassette. 1) The valve is connected to side port 10 of the pressurized cell culture cassette 11. 2) The sterile fluid reservoir 12 is prefilled with sterile fluid to the mean desired hydrostatic pressure. 3) The computer regulator or controller 13 is turned on. 4) The computer algorithm generates piston motion in the bi-directional computer-controlled syringe pump 14 to adjust the level within the fluid reservoir such that the level corresponds to the maximum and minimum hydrostatic pressure desired within the cassette. The intent is to simulate the variable hydrostatic pressure that the heart generates. The bi-directional computer-controlled syringe pump and the computer controller comprise a device for generating variable hydrostatic pressure within the cell cassette.
Figure 5:
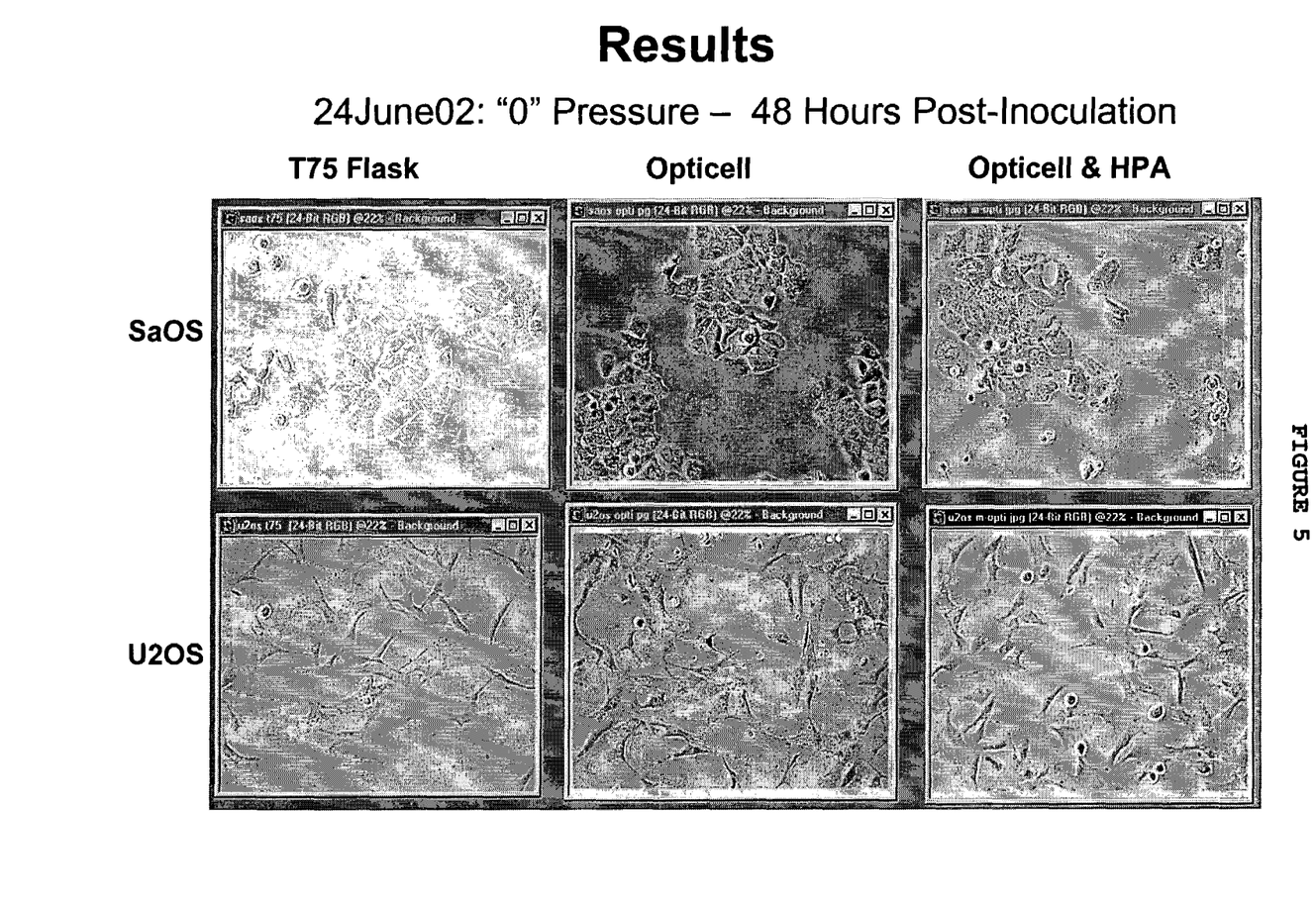
FIG. 5. Results at "0" Pressure, 48 Hours Post Inoculation. This figure shows the results of two different osteogenic sarcoma cell lines, SaOS and U2OS, 48 hours post inoculation using a T75 Flask, Opticell and Opticell with High-Pressure Apparatus.
Figure 6:
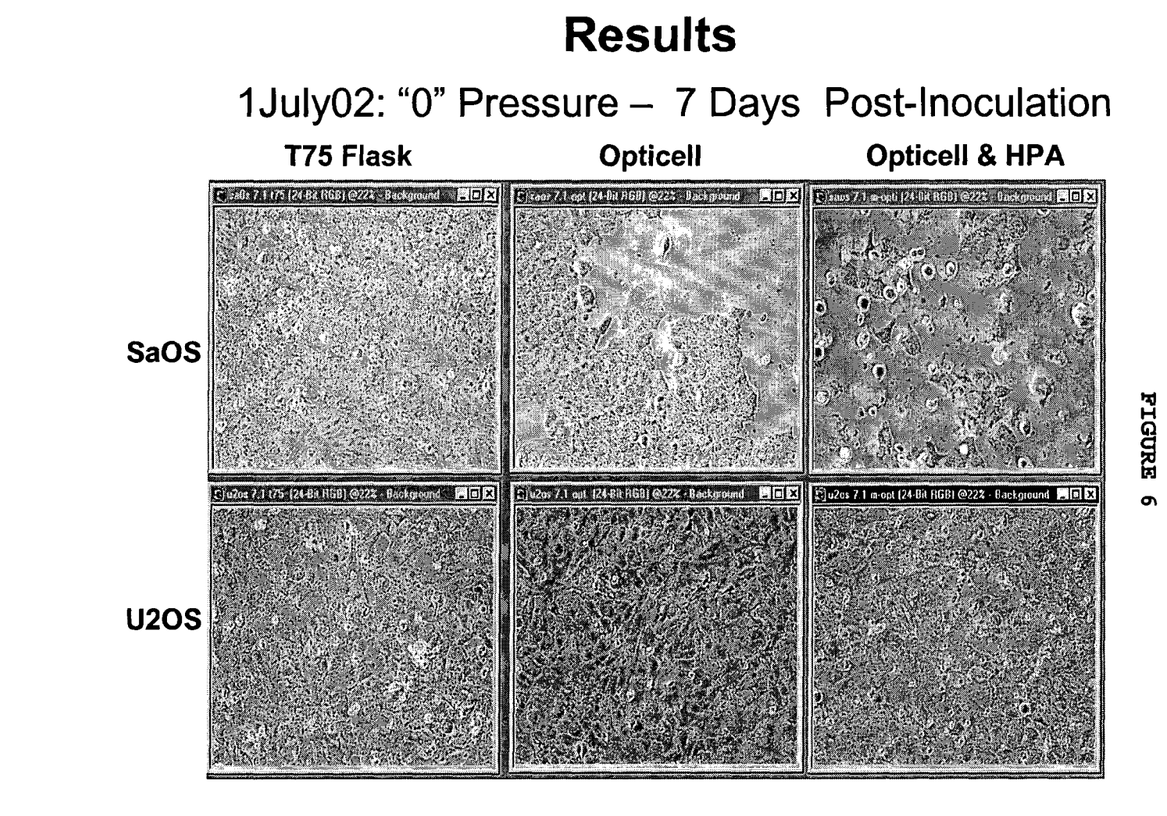
FIG. 6. Results at "0" Pressure, 7 Days Post Inoculation. This figure shows the results of two different osteogenic sarcoma cell lines, SaOS and U2OS, 7 days post inoculation using a T75 Flask, Opticell and Opticell with High-Pressure Apparatus.
Figure 7:
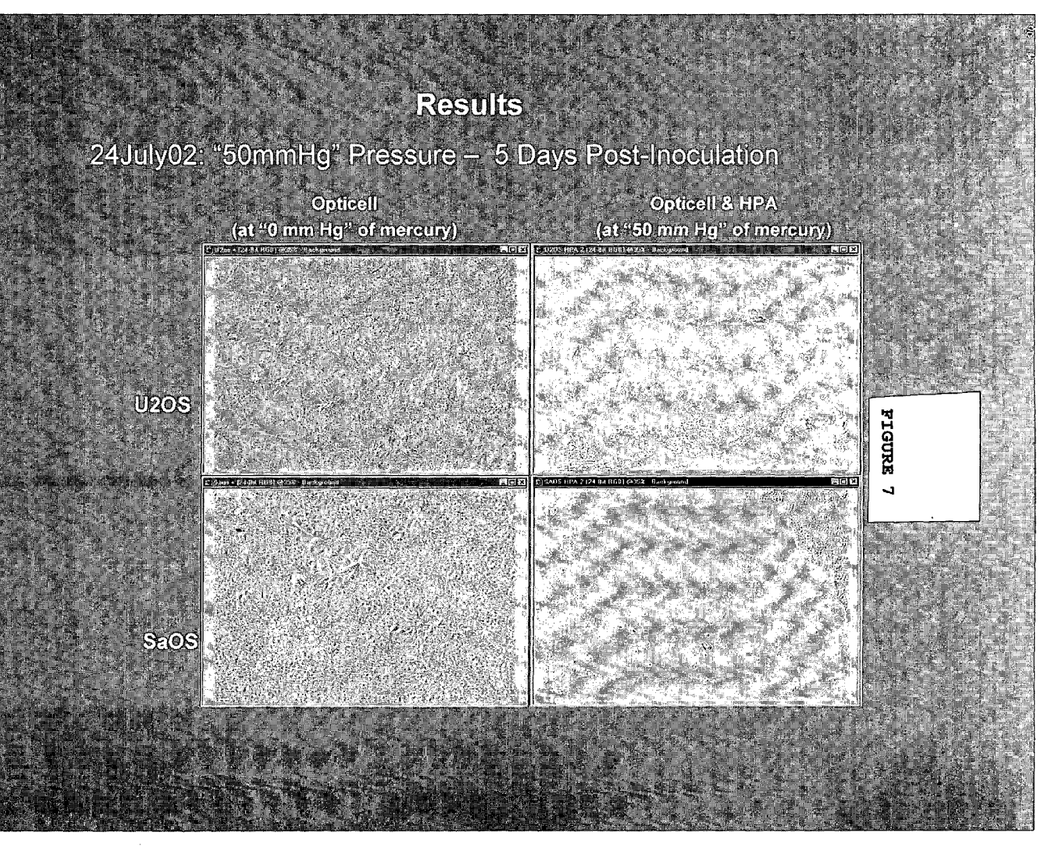
FIG. 7. Results at "50 mmHg" Pressure, 5 Days Post Inoculation. This figure shows the results of two different osteogenic sarcoma cell lines, U2OS and SaOS, 5 days post inoculation using Opticell at "0 mmHg" and Opticell with the High-Pressure Apparatus at "50 mmHg."
Figure 8A:
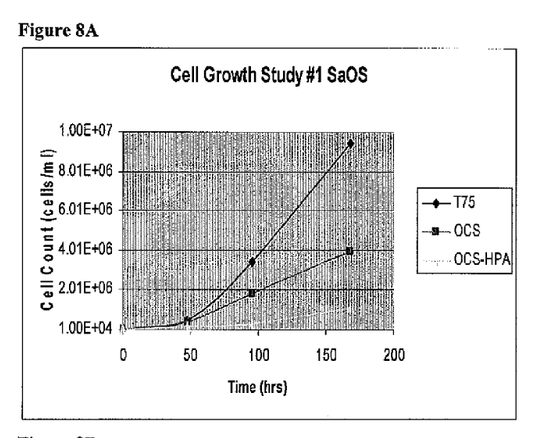
FIG. 8A. Study #1 shows total cell count. This baseline study compares cell growth using a standard T75 flask and cell growth using Opticell with and without the High-Pressure Apparatus.
Figure 8B:
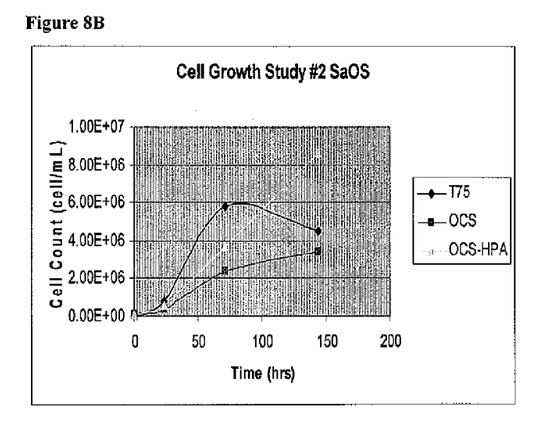
FIG. 8B. Study #2 repeats Study #1.
Figure 8C:
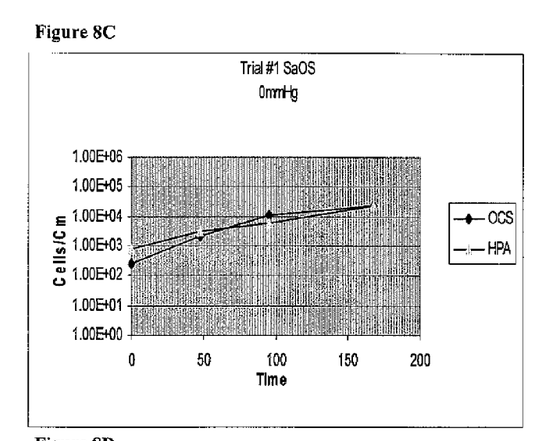
Figure 8D:
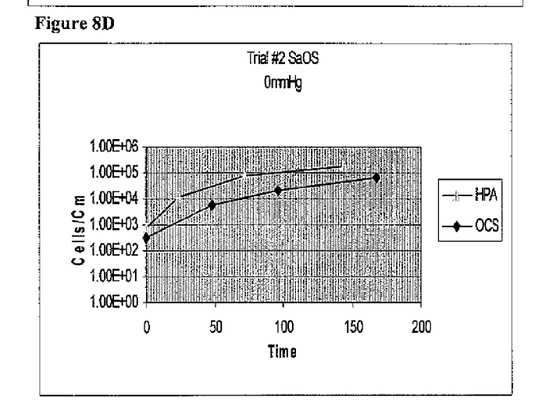
FIG. 8D. Trial #2 is a repeat of Trial #1. Same data as in 8B. No difference in cell count per $cm^2$ is observed in 8C and 8D.
Figure 9:
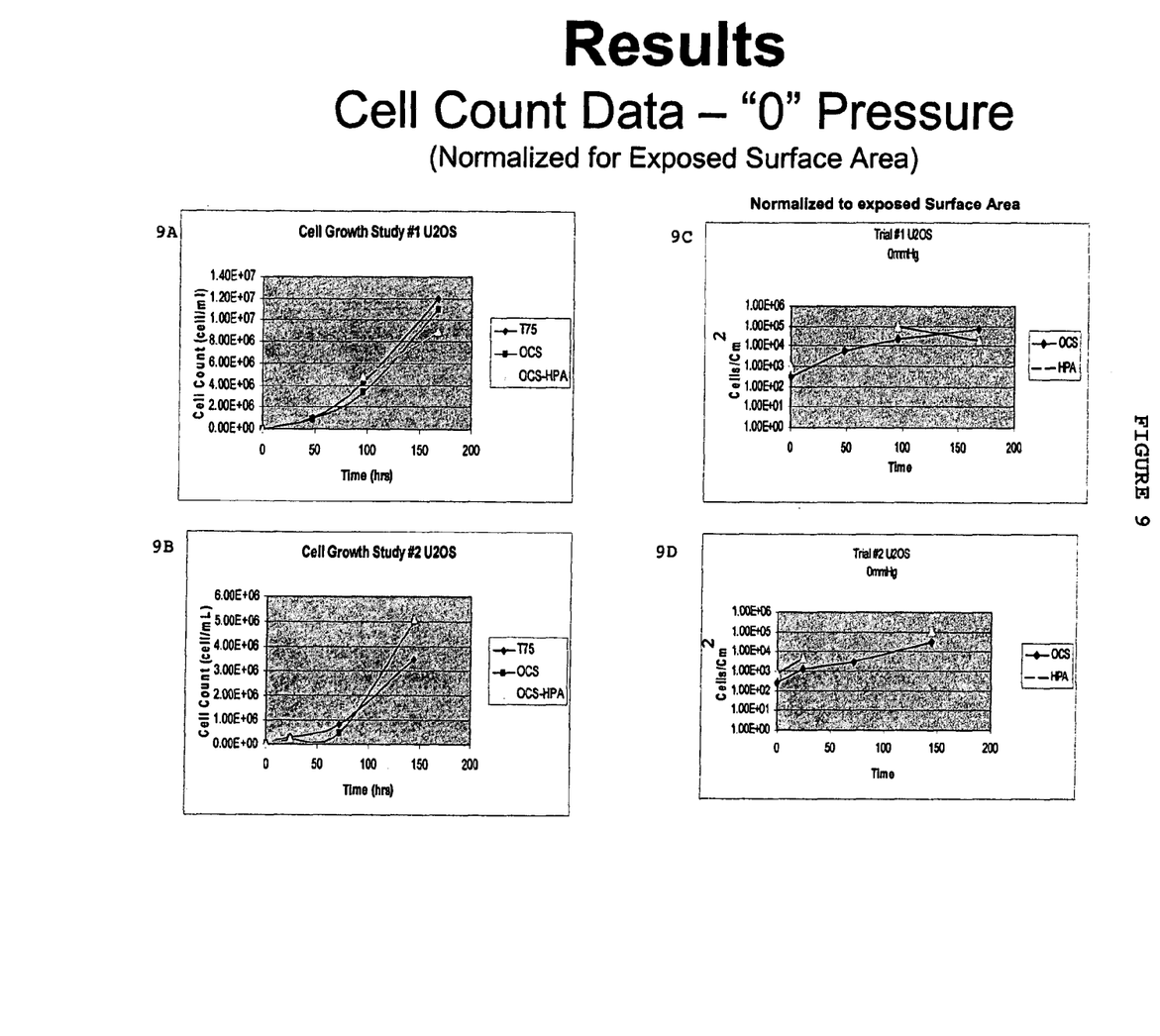
FIG. 9. Effect of Mesh on U2OS Growth Rate.
Figure 10A:
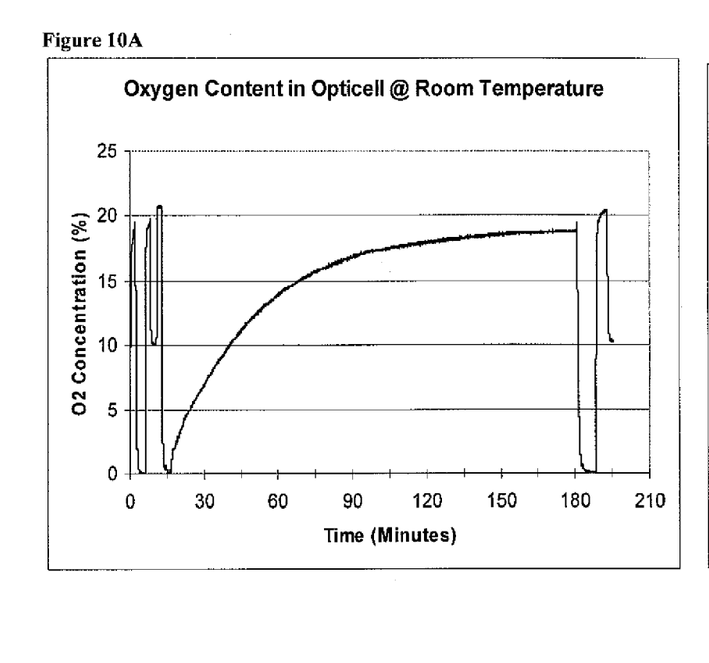
Figure 10B:
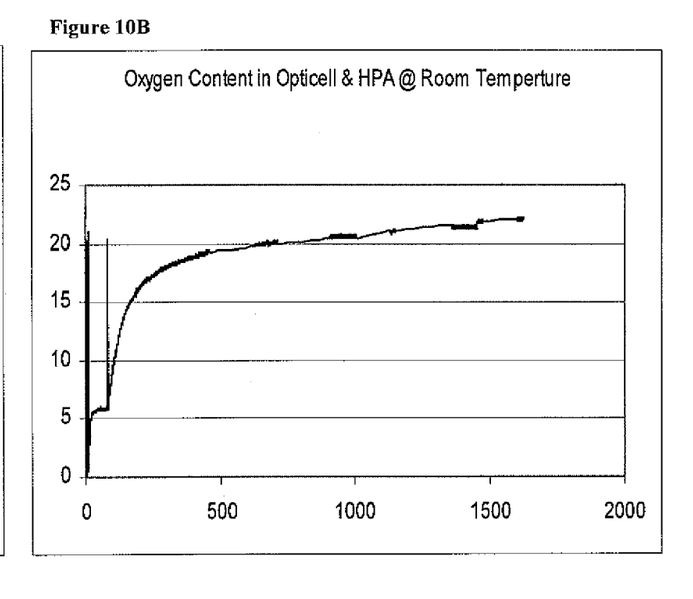

Pressure is provided to the 2-D cell culture cassette via a passive fluid reservoir or a computer controlled pressure regulator attached to the reservoir to create a static or variable pressure head, respectively to the growth media. In addition to simulating the in vivo elevated pressure conditions of growing tumors, pressure regulation also ensures that the media fluid volume within the cassette is constant as water evaporates across the membrane. FIG. 2 is a schematic drawing that shows the 2-D cell culture cassette and pressure regulation assembly. This approach is suggested because the outlet from one reservoir can be connected to a multi-port manifold and connected to several 2-D cell culture cassettes simultaneously. If a time varying pressure waveform is desired, the computerized pressure controller can add a time varying component to the static pressure head and simulate an in vivo pressure waveform. The regulator shown in the FIG. 4 utilizes an oscillating piston that adds or removes fluid from the reservoir to increase or decrease the static pressure head. This approach is one of many approaches that can be used to vary reservoir pressure. The "Connection Valve" permits connection of a 2-D cell culture cassette to the reservoir manifold and pressurization of the cassette when it is turned on. A second port or "Sampling Valve", installed on the opposite side of the cassette, can be used to obtain media samples for analysis or cell harvest. Gas and temperature regulation within the 2-D cell culture cassette is accomplished by placing the cassette and tubing within a temperature-controlled incubator with provision to accommodate pump tubing.

Operative Conditions:

The operating parameters that are adjusted to properly grow cells within the 2-D cell culture cassette with the pressure adapter or the new high pressure cassette installed include: 1) Fluid pressure applied to the 2-D cell culture media. This pressure is selected by the investigator based upon the experimental conditions desired and can range from negative to 100 mmHg (gauge). Pressure is adjusted using the height of the passive water head. The computerized pressure regulator can create a time varying pressure with a frequency of range of 0 to 2 Hz. 2) Gas mixture and temperature applied to the incubator: Both of these parameters depend upon conditions selected by the investigator and must be consistent with viability of cells and experimental design.

Uses and Applications:

The 2-D cell culture cassette high-pressure adapter is designed to enable the culture cassette to grow cells in a 2-D pressure-controlled environment; The high pressure cassette design can be used directly. In both, high pressure capability is especially important for solid tumor cells that grow under conditions of elevated interstitial fluid pressure. Applications for this invention include the determination of tumor cells' gene expression as a function of growth pressure, and to assess an individual patient's tumor chemo-sensitivity.

Advantages:

The problem that the adapter invention solves is growing 2-D tumor cells within a 2-D cell culture cassette at elevated pressures in a one atmosphere gas environment. The high-pressure design can accomplish the same high-pressure cell culture functionality without the need for additional hardware facilitating closer packing within growth incubators.

Disadvantages or Limitations:

The membrane exposure to ambient gases is reduced by the size of the openings provided by the pressure adapter's or high pressure cassettes' screen mesh.

To summarize, this invention provides the 2-D cell culture cassette consisting of a thin plastic case with two gas permeable membrane sides and two rubber infusion ports on the top of the cassette a safe means to culture cells under elevated fluid pressure. It has been successfully used for culturing a variety of single cell organisms under typical culture conditions. While it can be used to culture solid tumor cells, it is not suitable for simulating the in vivo growth conditions of solid tumor cells. These conditions typically include elevated and pulsatile interstitial pressures. Evidence suggests that the gene expression of these cells may be influenced by elevated interstitial pressure and this expression alters the cells' response to chemotherapy. When the 2-D cell culture cassette is filled with growth media and the media's internal pressure is raised to typical in vivo intra-tumoral pressures, the cassette's membrane walls bulge. The magnitude of the bulging, is related to the applied pressure and elasticity of the membrane. This bulging results in interior fluid volume changes and the potential for membrane rupture. In addition, the infusion port is subject to leaking following media delivery through the rubber within the port. The adapter described within this invention permits the 2-D cell culture cassette to be used under pressurized media conditions without changing its internal volume, eliminates infusion port leakage and provides support for valve assemblies to permit continual communication with the 2-D cell culture media for pressure maintenance, fluid sampling, etc. As an alternative, this invention introduces a design for a 2-D high-pressure cell culture cassette that incorporates the functionality of the high-pressure adapter with a low-pressure 2-D cassette.

Modification to 2-D Cell Culture Cassette:

Problem: The rubber bungs that come standard on the 2-D cell culture cassettes leak after needles, remaining in place for extended periods of time, are removed. Specifically, the phenomenon occurs after the 2-D cell culture cassettes have been in an 37° C. incubator for several days with the HPA and pressurization needles in place. The bungs were designed to seal after needle insertion and withdrawal. Long term contact in moist heated environment causes the rubber to accommodate to the needle's presence. When the needle is withdrawn, the insertion tract does not close resulting in loss of pressure and media contents.

Solution: Machine a hole suitable for an 18 gauge needle in the middle of the short side of the 2-D cell culture cassette frame. A luer valve fitting is fixed into this hole using waterproof epoxy or heat welding. When the cassette is to be pressurized tubing is attached to the valve and the valve is opened to allow pressurizing fluid to enter the cassette. When not needed the valve remains closed. The rubber bung access areas of the HPA remain available for brief injection/withdrawals without leaks.

The combination of the HPA and modified 2-D cell culture cassette has been used very successfully without leaks and is superior to using the HPA with standard 2-D cell culture cassette alone.

IMPT: The 2-D cell culture cassette cannot be fluid pressurized and used without fluid replenishment for extended periods of time because pressure drops from the evaporative loss of water vapor from within the cassette. This has been confirmed experimentally.

What is claimed is:

1. An apparatus far growing cells under static or variable pressure, comprising:
   a cell cassette comprising a case with two opposite gas-permeable membrane sides, and ports on top of the cassette, wherein cells can grow in culture media within the cell cassette; and a pressure adaptor having two side assemblies that are mirror images of one another and attached together by a hinge, each assembly comprising a frame around a rigid support, wherein the hinge enables the pressure adaptor to fold and hold in place the cell cassette between the two side assemblies, wherein the rigid supports of the pressure adaptor fit over the membranes of the cell cassette providing support to the membranes, maintaining the cell cassette at a constant volume when pressure is applied to the cassette, and preventing the membranes from bulging.

2. The apparatus of claim 1, wherein the cell cassette further comprises ports on the sides of the cassette.

3. The apparatus of claim 1, wherein the ports are configured to allow culture media to flow through the cell cassette.

4. The apparatus of claim 1, wherein one of the ports is provided with a luer valve or three-way valve.

5. The apparatus of claim 1, wherein the membrane is a fiber-reinforced membrane.

6. The apparatus of claim 5, wherein the fiber is metal or organic based.

7. The apparatus of claim 1, further comprising a device for generating variable hydrostatic pressure within the cell cassette, the device comprising a bi-directional computer-controlled syringe pump and a controller programmed to generate piston motion in the pump.

8. The apparatus of claim 1, wherein the rigid support is a mesh.

9. The apparatus of claim 8, wherein mesh is made of stainless steel.

10. The apparatus of claim 8, wherein mesh is made of plastic.

11. The apparatus of claim 8, wherein mesh is made of platinum, gold, titanium or biocompatible metal.

12. The apparatus of claim 8, wherein the mesh is adapted to generate an electric field across the cell cassette.

13. The apparatus of claim 8, wherein mesh is covering at least 50% of the membrane.

14. The apparatus of claim 7, wherein the device is adapted to control the pressure of one or more cell cassette.

15. The apparatus of claim 1, made of plastic or stainless steel.

16. The apparatus of claim 1, made of materials which can withstand high or negative pressure, and the heats of sterilization, or resist the oxidation of sterilizing gases.

* * * * *

UNITED STATES PATENT AND TRADEMARK OFFICE
CERTIFICATE OF CORRECTION

PATENT NO.        : 7,422,893 B2
APPLICATION NO.   : 10/378585
DATED             : September 9, 2008
INVENTOR(S)       : Gene R. Diresta, John H. Healey and Robert Schwar It is certified that error appears in the above-identified patent and that said Letters Patent is hereby corrected as shown below:

Title Page, item (73) Assignee:, "Memorial Sloan-Kettering Cancer Center" should be -- Sloan-Kettering Institute for Cancer Research --

Signed and Sealed this

Third Day of March, 2009

JOHN DOLL
*Acting Director of the United States Patent and Trademark Office*

UNITED STATES PATENT AND TRADEMARK OFFICE
CERTIFICATE OF CORRECTION

| | | |
|---|---|---|
| PATENT NO. | : 7,422,893 B2 | Page 1 of 1 |
| APPLICATION NO. | : 10/378585 | |
| DATED | : September 9, 2008 | |
| INVENTOR(S) | : Gene R. Diresta, John H. Healey and Robert Schwar | |

It is certified that error appears in the above-identified patent and that said Letters Patent is hereby corrected as shown below:

Please replace the paragraph that begins on col. 1, line 8 as follows:

-- This application was supported in part by a National Cancer Institute Core Grant No. 08748. Accordingly, the United States Government has certain rights in this invention. --

Signed and Sealed this

Fifth Day of May, 2009

JOHN DOLL
*Acting Director of the United States Patent and Trademark Office*